United States Patent
Perier et al.

(10) Patent No.: US 9,814,660 B2
(45) Date of Patent: Nov. 14, 2017

(54) COMPOSITION AND ASSOCIATION OF SUNSCREENS FOR PHOTOSTABILIZING BUTYL METHOXYDIBENZOYLMETHANE (BMDBM)

(71) Applicant: PIERRE FABRE DERMO-COSMETIQUE, Boulogne-Billancourt (FR)

(72) Inventors: Valérie Perier, Frouzins (FR); Hélène Dromigny, Toulouse (FR)

(73) Assignee: PIERRE FABRE DERMO-COSMETIQUE, Boulogne-Billancourt (FR)

( * ) Notice: Subject to any disclaimer, the term of this patent is extended or adjusted under 35 U.S.C. 154(b) by 0 days.

(21) Appl. No.: 14/375,731

(22) PCT Filed: Jan. 30, 2013

(86) PCT No.: PCT/EP2013/051777
§ 371 (c)(1),
(2) Date: Jul. 30, 2014

(87) PCT Pub. No.: WO2013/113746
PCT Pub. Date: Aug. 8, 2013

(65) Prior Publication Data
US 2015/0056150 A1 Feb. 26, 2015

(30) Foreign Application Priority Data

Jan. 31, 2012 (WO) .................. PCT/FR2012/050202

(51) Int. Cl.
| | | |
|---|---|---|
| *A61K 8/49* | (2006.01) | |
| *A61K 8/35* | (2006.01) | |
| *A61Q 17/04* | (2006.01) | |
| *A61K 31/4192* | (2006.01) | |
| *A61K 31/53* | (2006.01) | |
| *A61K 31/12* | (2006.01) | |

(52) U.S. Cl.
CPC .............. *A61K 8/4966* (2013.01); *A61K 8/35* (2013.01); *A61K 8/496* (2013.01); *A61K 31/12* (2013.01); *A61K 31/4192* (2013.01); *A61K 31/53* (2013.01); *A61Q 17/04* (2013.01); *A61K 2800/30* (2013.01)

(58) Field of Classification Search
None
See application file for complete search history.

(56) References Cited

U.S. PATENT DOCUMENTS

| | | |
|---|---|---|
| 6,419,908 B1 | 7/2002 | Candau et al. |
| 2003/0161849 A1* | 8/2003 | Heidenfelder et al. ....... 424/401 |
| 2003/0185770 A1 | 10/2003 | Birrenbach |
| 2005/0008587 A1 | 1/2005 | Schulz et al. |
| 2005/0013782 A1 | 1/2005 | Goppel et al. |
| 2008/0249172 A1 | 10/2008 | Ansmann et al. |
| 2010/0129303 A1* | 5/2010 | Dueva-Koganov ...... A61K 8/29 424/60 |

FOREIGN PATENT DOCUMENTS

| | | |
|---|---|---|
| DE | 101 35 258 A1 | 2/2003 |
| EP | 1 093 797 A1 | 4/2001 |
| EP | 1 291 010 A2 | 3/2003 |
| EP | 1 308 153 A2 | 5/2003 |
| EP | 1 764 081 A1 | 3/2007 |
| GB | 2 439 618 A | 1/2008 |
| JP | 2003-532665 A | 11/2003 |
| JP | 2005-513089 A | 5/2005 |
| JP | 2009-507971 A | 2/2009 |
| JP | 2009-518329 A | 5/2009 |
| WO | WO 02/43656 A2 | 6/2002 |
| WO | WO 03/039507 A1 | 5/2003 |
| WO | WO 2007/065574 A2 | 6/2007 |

OTHER PUBLICATIONS

International Search Report, dated Dec. 13, 2012, issued in International Application No. PCT/FR2012/050202.
International Search Report, issued in PCT/EP2013/051777, dated May 19, 2014.
Chatelain, E., et al, "Photostabilization of Butyl methoxydibenzoylmethane (Avobenzone) and Ethylhexyl methoxycinnamate by Bis-ethylhexyloxyphenol methoxyphenyl triazine (Tinosorb S), a New UV Broadband Filter," Photochemistry and Photobiology, 2001, vol. 74, No. 3, pp. 401-406.

* cited by examiner

Primary Examiner — Melissa Fisher
(74) Attorney, Agent, or Firm — Birch, Stewart, Kolasch & Birch, LLP

(57) ABSTRACT

The present invention concerns a composition containing a photostabilized combination of Butyl Methoxydibenzoylmethane (BMDBM), Bis-Ethylhexyloxyphenol Methoxyphenyl Triazine (BEMT), and Methylene Bis-Benzotriazolyl Tetramethylbutylphenol (MBBT) wherein: (i)—the BEMT/BMDBM mass ratio is greater than or equal to 1 and preferably greater than or equal to 1.5; (ii)—the content of BMDBM is comprised between 1% and 5% by weight with regard to the total weight of the composition; (iii)—the quantity of MBBT is comprised between 3% and 7% by weight with regard to the total weight of the composition, said combination containing no octocrylene, PABA or ethylhexyl methoxycinnamate, and a pharmaceutically or cosmetically acceptable excipient.

5 Claims, No Drawings

COMPOSITION AND ASSOCIATION OF SUNSCREENS FOR PHOTOSTABILIZING BUTYL METHOXYDIBENZOYLMETHANE (BMDBM)

The present invention concerns a combination of sunscreens for photostabilization of Butyl Methoxydibenzoylmethane (BMDBM).

Protection against UVA (320-400 nm) must be substantial to limit damage related to prolonged exposure that could lead to changes in the skin, acceleration of photoaging, loss of skin elasticity, etc.

First of all, we will review the nomenclature and abbreviations of the main filters involved in the scope of the present invention:

Butyl Methoxydibenzoylmethane (BMDBM) =avobenzone=CAS Registry Number: 70356-09-1, which filter is sold under the DSM trademark Parsol1789®, 2,4-Bis[4-(2-ethylhexyloxy)-2-hydroxyphenyl]-6-(4-methoxyphenyl)-1,3,5-triazine=Bis-Ethylhexyloxyphenol Methoxyphenyl Triazine (BEMT) Bemotrizinol=CAS Registry Number: 187393-00-6, which filter is sold under the BASF trademark Tinosorb S®, 2,2'-Methylene-bis-(6-(2H-benzotriazole-2-yl)-4-(1,1,3,3-tetramethylbutyl)-phenol=Methylene Bis-Benzotriazolyl Tetramethylbutylphenol (MBBT) =Bisoctrizole=CAS Registry Number: 103597-45-1, which filter is sold under the BASF trademark Tinosorb M®.

Butyl Methoxydibenzoylmethane (BMDBM) is not a UV radiation stable filter. A cleavage of the molecule takes place, which breaks down into various chemical elements with no absorbent activity.

In combination with other filters (for example ethylhexyl methoxycinnamate), BMDBM can still break down and lose its photoprotective properties.

BMDBM is often combined with octocrylene, which photostabilizes it, or even PABA® (para-aminobenzoic acid). However, octocrylene has the drawback of being a powerful allergen which causes contact eczema in children and cross allergies with ketoprofen.

More recently, the prior art includes document US20110212040 which teaches the stabilization of BMDBM by addition of synthetic or natural phytoene or phytofluene.

The goal of the present invention is to offer a new alternative for photostabilizing BMDBM while developing a photoprotective system according to current regulations.

The present invention concerns a combination containing Butyl Methoxydibenzoylmethane (BMDBM), Bis-Ethylhexyloxyphenol Methoxyphenyl Triazine (BEMT), and Methylene Bis-Benzotriazolyl Tetramethylbutylphenol (MBBT) characterized in that:
the BEMT/BMDBM mass ratio is greater than or equal to 1 and preferably greater than or equal to 1.5 and
said combination does not contain octocrylene.

The present invention concerns a composition containing a photostabilized combination of Butyl Methoxydibenzoylmethane (BMDBM), Bis-Ethylhexyloxyphenol Methoxyphenyl Triazine (BEMT), and Methylene Bis-Benzotriazolyl Tetramethylbutylphenol (MBBT), wherein:
i. the BEMT/BMDBM mass ratio is greater than or equal to 1 and preferably greater than or equal to 1.5 and
ii. the content of BMDBM is comprised between 1% and 5% by weight with regard to the total weight of the composition,
iii. the quantity of MBBT is comprised between 3% and 7% by weight with regard to the total weight of the composition,
said combination containing no octocrylene, PABA or ethylhexyl methoxycinnamate, and a pharmaceutically or cosmetically acceptable excipient.

In one particular embodiment of the invention, the BEMT/BMDBM mass ratio is less than or equal to 5, preferably less than or equal to 4 and even more preferentially less than or equal to 3.

Preferentially, the BEMT/BMDBM mass ratio will be chosen in the range from 1 to 5, preferentially 1.5 to 5 and even more preferentially 1.5 to 3.

According to another characteristic of the invention, the BEMT content is comprised between 2% and 6% by weight with regard to the total weight of the composition.

In the framework of the present invention, the BEMT/BMDBM mass ratio has to be considered as a predominantly characteristic feature. That means that the concentration of the different solar filters BEMT, BMDBM and MBBT will have to be adjusted within each concentration rate in order for said mass ratio to be first and foremost respected.

Another subject of the present invention concerns a composition containing a combination of BMDBM, BEMT and MBBT characterized in that:
the BEMT/BMDBM mass ratio is greater than or equal to 1 and preferably greater than or equal to 1.5 and
said combination does not contain octocrylene,
the quantity of MBBT is comprised between 3% and 7% by weight with regard to the total weight of the composition,
and with a pharmaceutically or cosmetically acceptable excipient.

Another subject of the present invention concerns a composition containing a combination of BMDBM, BEMT and MBBT characterized in that:
the BEMT/BMDBM mass ratio is greater than or equal to 1 and preferably greater than or equal to 1.5,
said combination contains no octocrylene, PABA or ethylhexyl methoxycinnamate.
the quantity of MBBT is comprised between 3% and 7% by weight with regard to the total weight of the composition,
and with a pharmaceutically or cosmetically acceptable excipient.

According to another characteristic of the present invention, the composition above also has a content of Bis-Ethylhexyloxyphenol Methoxyphenyl Triazine (BEMT) comprised between 2 and 6% by weight with regard to the total weight of the composition.

According to another characteristic of the present invention, the composition above also has a content of Butyl Methoxydibenzoylmethane (BMDBM) comprised between 1 and 5% by weight with regard to the total weight of the composition.

Finally, according to another characteristic of the present invention, the composition above also has another filter, preferably between 1 and 10% by weight with regard to the total weight of the composition.

According to another aspect, the invention also concerns the use of a combination of Butyl Methoxydibenzoylmethane (BMDBM) Bis-Ethylhexyloxyphenol Methoxyphenyl Triazine (BEMT), and Methylene Bis-Benzotriazolyl Tetramethylbutylphenol (MBBT), in which the BEMT/BM- DBM mass ratio is greater than or equal to 1 and preferably greater than or equal to 1.5, and in the absence of octocrylene, PABA and ethylhexyl methoxycinnamate to photostabilize BMDBM in a photoprotective composition.

"Photostabilization, photostable or photostability" mean, in the sense of the present invention, that after irradiation of 5 MED and preferably 10 MED, the following is retained:
- at least 80% and preferably at least 85% and even more preferentially at least 90% of the total SPF (290 to 400 nm); and
- at least 80% and preferably at least 85% and even more preferentially at least 90% for the UVA part (320 to 400 nm) of the total SPF.

Preferably, the combination or composition according to the present invention also contains no PAPA®.

Combinations according to the present invention represent photostable photoprotective systems combining organic fat-soluble filters (such as BMDBM and BEMT) which are perfectly and evenly distributed on the skin and organic screens (like MBBT) dispersed in the aqueous phase for a better absorption response and therefore better efficacy.

Preferably, the compositions according to the present invention are adjusted so as to obtain a photoprotective system:
- having the broadest possible UV absorption spectrum (maximum spectral coverage of 290 to 400 nm)
- according to current regulations, that is having a critical wavelength λc greater than or equal to 370 nm and an SPF/UVA ratio less than or equal to 3.

More preferentially, the composition according to the present invention may correspond to the maximum category in terms of sun protection, that is, having SPF 50+.

One or more of the following UVB filters can be added to the composition according to the invention:
- Salicylates: Homosalate, ethylhexyl salicylate
- Phenylbenzimidazole Sulfonic Acid
- Ethylhexyl Triazone, Diethylhexyl Butamido Triazone
- TiO2
- Tris-biphenyl triazine.

The UVB filters indicated above are UVB filters considered satisfactory from the point of view of tolerance, toxicity, photostabilization and UV absorption. Thus, as a precaution regarding homosalate, preferably the following UVB filter or filters are preferred:
- Ethylhexyl salicylate
- Phenylbenzimidazole Sulfonic Acid
- Ethylhexyl Triazone, Diethylhexyl Butamido Triazone
- TiO2
- Tris-biphenyl triazine.

Furthermore, the composition will preferentially be stable to light, air, humidity and temperature.

Another subject of the present invention concerns a composition containing a photostabilized combination comprising
Butyl Methoxydibenzoylmethane (BMDBM), Bis-Ethylhexyloxyphenol Methoxyphenyl Triazine (BEMT), and Methylene Bis-Benzotriazolyl Tetramethylbutylphenol (MBBT) wherein:
i. the BEMT/BMDBM mass ratio is greater than or equal to 1 and preferably greater than or equal to 1.5 and
ii. the content of BMDBM is comprised between 1% and 5% by weight with regard to the total weight of the composition,
iii. the quantity of MBBT is comprised between 3% and 7% by weight with regard to the total weight of the composition, in addition, one or more UVB filters chosen from among the following filters:
- Ethylhexyl salicylate
- Phenylbenzimidazole Sulfonic Acid
- Ethylhexyl Triazone, Diethylhexyl Butamido Triazone
- TiO2
- Tris-biphenyl triazine and a pharmaceutically or cosmetically acceptable excipient.

In one particular embodiment of the invention, the quantity of the UVB filter or filters is comprised in total between 1 and 10% by weight with regard to the weight of the composition.

In another embodiment of the invention, the composition contains a single additional UVB filter in an amount of 1% to 10% by weight with regard to the weight of the composition and preferably in an amount of 1% to 5% by weight with regard to the weight of the composition.

In one particular embodiment of the invention, the composition will contain a single UVB filter chosen from among the following filters:
- Ethylhexyl salicylate
- Phenylbenzimidazole Sulfonic Acid
- Ethylhexyl Triazone, Diethylhexyl Butamido Triazone
- TiO2
- Tris-biphenyl triazine The present invention finally concerns the use of a combination containing:
Butyl Methoxydibenzoylmethane (BMDBM), Bis-Ethylhexyloxyphenol Methoxyphenyl Triazine (BEMT), and Methylene Bis-Benzotriazolyl Tetramethylbutylphenol (MBBT), in which the BEMT/BMDBM mass ratio is greater than or equal to 1 and preferably greater than or equal to 1.5,
one or more UVB filters chosen from among the following filters and preferably only 1 UVB filter chosen from among the following filters:
- Ethylhexyl salicylate
- Phenylbenzimidazole Sulfonic Acid
- Ethylhexyl Triazone, Diethylhexyl Butamido Triazone
- TiO2
- Tris-biphenyl triazine to photostabilize BMDBM in a photoprotective composition.

"Pharmaceutically or cosmetically acceptable excipient" means any adjuvant or excipient for manufacturing, preserving or administering the composition.

Compositions according to the invention may more particularly be sunscreen compositions. They are particularly intended for protecting skin (face and/or body) and/or hair from ultraviolet radiation.

The present invention also concerns a method for protecting skin (face and/or body) and/or hair from ultraviolet radiation comprising applying a composition described previously onto the skin (face and/or body) and/or hair.

Compositions according to the invention may also comprise conventional cosmetic or pharmaceutical adjuvants, in particular chosen from among fats, organic solvents, thickeners, softeners, opacifiers, stabilizers, emollients, antifoaming agents moisturizers, fragrances, preservatives, polymers, fillers, sequestering agents, bactericides, odor absorbers, basifying or acidifying agents, surfactants, free-radical scavengers, antioxidants, vitamins E and C, alpha-hydroxy acids or any other ingredient usually used in cosmetics or pharmaceuticals, particularly for the manufacture of sunscreen compositions.

The fats may consist of an oil or wax or mixtures thereof, and they also include fatty acids, fatty alcohols and fatty acid esters. The oils may be chosen from among animal, vegetable, mineral or synthetic oils and notably Vaseline oil, paraffin oil, volatile or nonvolatile silicone oil, isoparaffins, polyolefins and fluorinated and perfluorinated oils. Likewise, the waxes may be chosen from among animal, fossil, vegetable or synthetic waxes such as beeswax, candelilla wax, carnauba wax, petroleum wax (or microcrystalline wax), paraffin, and mixtures thereof.

The composition may further comprise a water-miscible polyol at room temperature (around 25° C.), in particular chosen from among polyols having from 2 to 20 carbon atoms, preferably having 2 to 10 carbon atoms, and preferentially having 2 to 6 carbon atoms, such as glycerin; glycol derivatives such as propylene glycol, butylene glycol, pentylene glycol, hexylene glycol, dipropylene glycol and diethylene glycol; glycol ethers such as C1-C4 alkyl ethers of mono-, di- or tri-propylene glycol, C1-C4 alkyl ethers of mono-, di- or triethylene glycol and mixtures thereof.

The composition may also comprise thickeners or rheology modifying agents, such as, for example, nonionic ethoxylated hydrophobically modified urethanes, polycarboxylic acid thickeners such as acrylates/steareth 20 methacrylate copolymers, carbomers, crosslinked acrylate copolymers and mixtures thereof.

The composition may also comprise acids and bases to adjust the pH zone of said composition. The bases may be mineral (sodium hydroxide, potassium hydroxide, ammonia, etc.) or organic such as mono-, di- or triethanolamine, aminomethylpropanediol, N-methylglucamine, basic amino acids such as arginine and lysine, and mixtures thereof.

The composition may also comprise skin conditioners. Examples of skin conditioners include, but are not limited to, anionic, cationic and nonionic surfactants such as sodium lauryl sulfate, sodium dioctyl sulfosuccinate, sodium stearate, ester sorbitan, ethoxylated fatty acids, ethoxylated fatty alcohols such as trideceth-9 and PEG-5 ethylhexanoate; any other emulsifier and conditioning agent known to the skilled person, and mixtures thereof.

Compositions according to the invention may further comprise additional active agents chosen in particular from among from moisturizers, desquamating agents, agents for improving barrier function, depigmenting agents, antioxidants, skin tighteners, anti-glycation agents, agents stimulating the synthesis of dermal and/or epidermal macromolecules and/or preventing their degradation, agents stimulating fibroblast or keratinocyte proliferation and/or keratinocyte differentiation, NO synthase inhibitors, agents increasing the activity of the sebaceous gland, tensioning agents, lipo-restructuring agents, slimming agents, agents promoting skin microcirculation, soothing and/or irritant agents, sebo-regulating or anti-seborrheic agents, astringents, wound healing agents, anti-inflammatory agents, anti-acne agents, and mixtures thereof.

Compositions according to the invention may be presented in any appropriate form for topical application, especially on the skin and/or hair. In particular, they may be in the form of emulsions obtained by dispersing a fatty phase in an aqueous phase, for example one or multiple oil-in-water or water-in-oil emulsions, or in the form of a gel or an anhydrous liquid, pasty or solid product, or in the form of a dispersion in the presence of spherules. Compositions according to the invention may also be less fluid and may be in the form of a white or colored cream, ointment, milk, lotion, serum, paste, mask, powder, solid stick or optionally, an aerosol, foam or spray. These compositions may also be water resistant.

In Vitro Method of Evaluating Total UV and UVA Photostability

A) Material

UV spectrophotometer:

The spectrophotometer measures the spectral transmittance through a plate with and without a layer of a sunscreen composition on its surface.

The spectrophotometer should allow measurements comprised between 290 nm and 400 nm. To reduce variability between measurement readings and to compensate for the lack of uniformity of the product layer, it is recommended that the reading zone of the sites be at least $0.5$ $cm^2$.

The spectrophotometer used for these measurements is the Labsphere® UV-1000S or 2000S.

Plate:

The plate is the material onto which the sunscreen composition is applied. This material must be transparent to UV, non-fluorescent, photostable and inert with regard to the compounds of the compositions tested. For this protocol, polymethyl methacrylate (PMMA) plates proved ideal.

UV Source:

The UV source is a solar simulator with a xenon arc lamp diffusing a visible+UVA+UVB spectrum. The UV source used for this study is Suntest CPS+ (Atlas).

B) Method:

Measuring transmission through an untreated plate:

Firstly, it is necessary to determine UV transmission through a control plate. This is prepared by spreading a few microliters of glycerin so that the surface of the plate is completely covered.

Sample application:

The sample to be tested is applied onto the PMMA plate in an amount of $1.3$ $mg/cm^2$ (actual quantity remaining on the plate). To guarantee the accuracy of the amount and the reproducibility of the results, the application zone is larger than $10$ $cm^2$.

The sample to be tested is applied in the form of a large number of small drops of the same volume, distributed over the entire surface of the plate.

In order to ensure that the quantity of the product is correct, a method of validating the quantity of product applied must be adopted (for example: weigh the plate before and after application of the product).

After application of the defined quantity of sample, the sample should be spread over the entire plate as quickly as possible (less than 30 seconds).

The sample is then placed for 15 minutes in the dark at room temperature in order to promote the formation of a homogenous film.

Measuring transmission through a plate treated with a sample:

The plate treated with the sample is analyzed with the spectrophotometer and the mean value of UV radiation transmission through the sample is determined for each wavelength from 290 nm to 400 nm (using the monochromatic absorbance data measured on the different areas of the plate).

Number of measurements:

At least three PMMA plates should be prepared for each sample. Each plate should be measured in at least nine different regions unless almost the entire surface is measured by spectrophotometry.

C) Calculation of Photostability:

Calculation of SPF and UVA (PPD) in vitro from absorbance data $A(\lambda)$ before and after irradiation with doses of 5 and 10 MED.

$$SPF \text{ in vitro} = \frac{\int_{\lambda=290\ nm}^{\lambda=400\ nm} E(\lambda) * S(\lambda) * d\lambda}{\int_{\lambda=290\ nm}^{\lambda=400\ nm} E(\lambda) * S(\lambda) * 10^{-A(\lambda)} * d\lambda}$$

Wherein:
$E(\lambda)$=Erythemal effectiveness spectrum
$S(\lambda)$=Solar spectral irradiance
$A(\lambda)$=Sample absorbance
$d\lambda$=Wavelength variation (1 nm)

$$PPD \text{ in vitro} = \frac{\int_{\lambda=320\ nm}^{\lambda=400\ nm} P(\lambda) * I(\lambda) * d\lambda}{\int_{\lambda=320\ nm}^{\lambda=400\ nm} P(\lambda) * I(\lambda) * 10^{-A(\lambda)} * d\lambda}$$

Wherein:
$P(\lambda)$=PPD action spectrum (Persistent Pigment Darkening)
$I(\lambda)$=Solar spectral irradiance
$A(\lambda)$=Sample absorbance
$d\lambda$=Wavelength variation (1 nm)

Calculation of photostability from the following formulas:

$$\text{Total } UV \text{ photostability} = \frac{SPF \text{ before irradiation}}{SPF \text{ after irradiation}}$$

$$UVA \text{ photostability} = \frac{PPD \text{ before irradiation}}{PPD \text{ after irradiation}}$$

COMPOSITION EXAMPLES

Composition 1

| Ingredients | % |
| --- | --- |
| Butyl Methoxydibenzoylmethane | 1-5 |
| Bis-Ethylhexyloxyphenol Methoxyphenyl Triazine | 2-6 |
| Methylene Bis-Benzotriazolyl Tetramethylbutylphenol | 3-7 |
| Glycerin | 10.0 |
| Demineralized water | QSP 100 |
| Na2EDTA | 0.1 |
| Xanthan gum | 0.3 |
| C12-C15 alkyl benzoate | 25.0 |
| Preservatives | qs |
| Stearyl alcohol | 2.5 |
| Glycerol monostearate | 2.5 |
| Potassium cetyl phosphate | 1.8 |

Composition 2

| Ingredients | % |
| --- | --- |
| Butyl Methoxydibenzoylmethane | 1-5 |
| Bis-Ethylhexyloxyphenol Methoxyphenyl Triazine | 2-6 |
| Methylene Bis-Benzotriazolyl Tetramethylbutylphenol UVB filter | 3-7 1-10 |
| Glycerin | 10.0 |
| Demineralized water | QSP 100 |
| Na2EDTA | 0.1 |
| Xanthan gum | 0.3 |
| C12-C15 alkyl benzoate | 25.0 |
| Preservatives | qs |
| Stearyl alcohol | 2.5 |
| Glycerol monostearate | 2.5 |
| Potassium cetyl phosphate | 1.8 |

Photostability Results

| Photostability: | Composition 1 | Composition 2 |
| --- | --- | --- |
| Total UV-5 MED | 96% | 93% |
| UVA-5 MED | 95% | 92% |
| Total UV-10 MED | 92% | 90% |
| UVA-10 MED | 91% | 89% |

The invention claimed is:

1. A composition comprising a pharmaceutically or cosmetically acceptable excipient, and a photostabilized combination of UVA and UVB filters consisting of
   (1) butyl methoxydibenzoylmethane (BMDBM),
   (2) bis-ethylhexyloxyphenol methoxyphenyl triazine (BEMT),
   (3) methylene bis-benzotriazolyl tetramethylbutylphenol (MBBT), and
   (4) a single additional UVB filter present in an amount of 1% to 10% by weight with regard to the weight of the composition, with the proviso that said single additional UVB filter is different from octocrylene, para-aminobenzoic acid (PABA), and ethylhexyl methoxycinnamate, wherein:
   i. the content of BEMT is comprised between 2% and 6% by weight with regard to the total weight of the composition,
   ii. the content of BMDBM is between 1% and 5% by weight with regard to the total weight of the composition,
   iii. the BEMT/BMDBM mass ratio is greater than or equal to 1.5 but less than or equal to 3, and
   iv. the quantity of MBBT is between 3% and 7% by weight with regard to the total weight of the composition.

2. The composition according to claim 1, wherein the single additional UVB filter is present in an amount of 1% to 5% by weight in all with regard to the weight of the composition.

3. The composition according to claim 1, wherein the single additional filter is a UVB filter that is selected from the group consisting of:
   ethylhexyl salicylate;
   phenylbenzimidazole sulfonic acid;
   ethylhexyl triazone;
   diethylhexyl butamido triazone;
   $TiO_2$; and
   tris-biphenyl triazine.

4. The composition according to claim 2, wherein the single additional filter is a UVB filter that is selected from the group consisting of:
ethylhexyl salicylate;
phenylbenzimidazole sulfonic acid;
ethylhexyl triazone;
diethylhexyl butamido triazone;
$TiO_2$; and
tris-biphenyl triazine.

5. A photoprotective system comprising the composition according to claim 1.

* * * * *